US007060687B2

(12) United States Patent
Hsu et al.

(10) Patent No.: US 7,060,687 B2
(45) Date of Patent: Jun. 13, 2006

(54) LIVE VACCINES FOR ALLERGY TREATMENT

(75) Inventors: Ching-Hsiang Hsu, Taibao (TW); Yuh-Chyang Charng, Taipei (TW)

(73) Assignee: Genmont Biotechnology Co., Chiayi (TW)

( * ) Notice: Subject to any disclaimer, the term of this patent is extended or adjusted under 35 U.S.C. 154(b) by 0 days.

(21) Appl. No.: 09/778,672

(22) Filed: Feb. 7, 2001

(65) Prior Publication Data

US 2002/0146429 A1 Oct. 10, 2002

(51) Int. Cl.
*A61K 48/00* (2006.01)
*A01N 65/00* (2006.01)
*A01N 63/00* (2006.01)
*C12N 15/74* (2006.01)
*C12P 21/06* (2006.01)

(52) U.S. Cl. .............. 514/44; 424/93.1; 424/93.2; 435/320.1; 435/69.1

(58) Field of Classification Search .............. 514/44; 424/93.21; 435/320.1
See application file for complete search history.

(56) References Cited

U.S. PATENT DOCUMENTS

| | | | |
|---|---|---|---|
| 5,032,399 | A | 7/1991 | Gorbach et al. |
| 5,494,664 | A | 2/1996 | Brassart et al. |
| 5,556,953 | A | 9/1996 | Zhang et al. |
| 5,698,204 | A | 12/1997 | Rogers et al. |
| 5,709,857 | A | 1/1998 | Morelli et al. |
| 5,776,761 | A | 7/1998 | Rogers et al. |
| 5,814,345 | A | 9/1998 | Beck et al. |
| 5,869,333 | A | 2/1999 | Singh et al. |
| 5,888,799 | A | 3/1999 | Curtiss, III .............. 435/252.3 |
| 5,939,283 | A | 8/1999 | Morgenstern et al. |
| 5,951,984 | A | 9/1999 | Kaneko et al. |
| 5,958,891 | A * | 9/1999 | Hsu et al. |
| 6,048,962 | A | 4/2000 | Gefter et al. |
| 6,077,517 | A | 6/2000 | Thomas et al. |
| 6,100,388 | A * | 8/2000 | Casas et al. |
| 6,110,898 | A * | 8/2000 | Malone et al. .............. 514/44 |
| 6,180,368 | B1 | 1/2001 | Singh et al. |
| 6,413,738 | B1 | 7/2002 | Thomas et al. |
| 6,737,521 | B1 * | 5/2004 | Fischetti et al. .............. 536/23.4 |

FOREIGN PATENT DOCUMENTS

| | | |
|---|---|---|
| CN | 1387442 | 12/2002 |
| NL | 8700890 | 11/1988 |
| WO | WO 92/00756 | 1/1992 |
| WO | WO 95/35389 | 12/1995 |
| WO | WO 97/14802 | 4/1997 |
| WO | WO 00/35484 | 6/2000 |
| WO | WO 00/52154 | 9/2000 |
| WO | WO 01/34186 | 5/2001 |
| WO | WO 01/66136 | 9/2001 |

OTHER PUBLICATIONS

Kailasapathy et al. Survival and therapeutic potential of probiotic organisms with reference to *Lacrobacillus acidophilus* and Bifidobacterium spp. pp. 80-88 1999.*
Janeway Jr., Immunobiology, 1999.*
Pouwels et al, Intl J Food Microbial 1998:41:155-67.*
Janeway Jr., Immunobiology, 2001, §14-25.*
Jahn-Schmid et al, Immunotechnol 1996;2: 103-13.*
Aas et al., "Standardization of Allergen Extracts with Appropriate Methods," *Allergy* 33:130-137 (1978).
Goldin et al., "Health benefits of probiotics," *Br. Jour. Nut.* 80:S203-S207 (1998).
Hakkaart et al, "Expression of the house dust mite allergen Der p 2 in the baker's yeast *Saccharomyces cerevisiae*," *Blackwell Science Ltd.* 28:45-52 (1998).
Hsu et al., "Inhibition of specific IgE response in vivo by allergen-gen transfer," *International Immunology*, 8:1405-1411 (1996).
Kailasapathy et al., "Survival and therapeutic potential of probiotic organisms with reference to *Lactobacillus acidophilus* and *Bifidobacterium* spp.," *J. Immunol. Cell Biol.* 78:80-88 (2000).
Lin et al., "Characterization of Der p V allergen, cDNA analysis, and IgE-mediated reactivity to the recombinant protein," *J. Allergy Clin. Immunol.* 94:6:989-996 (1994).
Pouwels et al., "The potential of *Lactobacillus* as a carrier for oral immunization: Development and preliminary characterization of vector systems for targeted delivery of antigens," *Jour. of Biotechnology* 44:183-192 (1996).
Salminen et al. "Functional food science and gastrointestinal physiology and function," *Br. J. Neutr.* 80:S147-S171 (1998).
Fischetti, et al., "Expression of foreign proteins on Gram-positive commensal bacteria for mucosal vaccine delivery," *Current Opinion in Biotechnology* 4, 603-610 (1993).
Hoyne, et al., "Characterization of T-cell responses to the house dust mite allergen Der p II in mice. Evidence for major and cryptic epitopes," *Immunology* 78 65-73 (1993).
Hoyne et al., Regulation of house dust mite responses by intranasally administered peptide: transient activation of CD4+ T cells precedes the development of tolerance *in vivo International Immunology* 8:3, 335-342 (1996).
Hoyne, et al., "Inhibition of T Cell and Antibody Responses to House Dust Mite Allergen by Inhalation of the Dominant T Cell Epitope in Naïve and Sensitized Mice," *J. Exp. Med* 178, 1783-1788 (1993).

(Continued)

*Primary Examiner*—Q. Janice Li
(74) *Attorney, Agent, or Firm*—Fish & Richardson P.C.

(57) ABSTRACT

The invention relates to transformed bacteria of the genus *Lactobacillus* or *Streptococcus*, the bacteria having a DNA molecule that includes (1) a nucleotide sequence that encodes a protein allergen and (2) a promoter operably linked to the nucleotide sequence.

24 Claims, 2 Drawing Sheets

OTHER PUBLICATIONS

Hsu, et al., Immunoprophylaxis of allergen-induced immunoglobulin E synthesis and airway hyperresponsiveness in vivo by genetic immunization, *Nature Medicine* 2:5 (1996).

Kato, et al., "Suppressive Effects of the Oral Administration of *Lactobacillus casel* on Type II Collagen-Induced Arthritis in DBA/1 Mice," *Life Sciences* 63:8, 635-644 (1998).

Kruisselbrink, et al., "Recombinant *Lactobacillus plantarum* inhibitis house dust mite-speicific T-Cell responses," *Clin. Exp. Imunol.* 126, 2-8 (2001).

Medaglini, et al., "Mucosal and systemic immune responses to a recombinant protein expressed on the surface of the oral commensal bacterium *Streptococcus gordonii* after oral colonization," *Proc. Natl. Acad. Sci.*, 92, 6868-6872 (1995).

Moffatt, et al., "Naked DNA: New shots for allergy?," Nature Medicine 2:5 (1996).

Cosgrove et al., "Group I allergens of grass pollen as cell wall loosening agents", *Proc. Natl. Acad. USA* 94:6559-6564 (1997).

Chew et al., "Allergenic differences between the domestic mites *Blomia tropicalis* and *Dermatophagoides pteronyssinus*", *Clin Exp Allergy* 29:982-988 (1999).

Fasler J. Allergy Clin Immunology 101(4):521-530, Apr. 1998.

Sato et al. Immunology 95(2):193-9, Oct. 1998.

* cited by examiner

LIVE VACCINES FOR ALLERGY TREATMENT

BACKGROUND OF THE INVENTION

Yogurt contains a variety of bacteria (often called lactic acid bacteria) that are not pathogenic in healthy individuals who have consumed the yogurt. These bacteria include members of the genera *Lactobacillus, Bifidobaterium,* and *Streptococcus.* It has been speculated that some of these bacteria may be useful as live oral vaccines. See, e.g., Pouwels et al., J. Biotechnol. 44:183–192, 1996. However, evidence that such live oral vaccines can be efficaciously used in the treatment or prevention of specific diseases or conditions has been lacking.

SUMMARY OF THE INVENTION

The invention is based on the discovery that recombinant lactic acid bacteria expressing a protein allergen can induce immunological tolerance against the allergen in animal models. In addition, this tolerance was sufficient to reduce symptoms associated with exposure to the allergen, such as airway hyperreactivity and inflammation. Given the high level of unpredictability in the art of live recombinant vaccines, this successful result was unexpected.

Accordingly, the invention features a transformed lactic acid bacterium, the bacterium having a DNA molecule that includes (1) a nucleotide sequence that encodes a protein allergen and (2) a promoter operably linked to the nucleotide sequence (i.e., positioned to express the allergen). The bacterium can be a member of lactic acid bacteria such as a member of the genus *Lactobacillus* (e.g., *L. acidophilus, L. casei, L. plantarum, L. fermentum, L. delbrueckii, L. johnsonii* LJI, *L. reuteri,* and *L. bulgaricus*), a member of the genus *Streptococcus* (e.g., *S. thermophilus*), or a member of the genus *Bifidobaterium* (e.g., *B. infantis, B. bifidum, B. longum, B. pseudolongum, B. breve, B. lactis* Bb-12, and *B. adolescentis*). The bacterium can also be *Lactobacillus* GG, which refers to probiotics as described in Salminen et al. Br. J. Neutr. 80:147–171, 1998. The allergen can be an allergen from a common dust mite, such as *Dermatophagoides pteronyssinus, D. farinae, D. microceras, Tyrophagus putesentiae, Lepidoglyphus domesticus, L. destructor, Acarus siro, Euroglyphus maynei,* and *Biomia tropicalis*; or other airborne allergen (aeroallergen) such as pollens, molds, animal dander, and insects. Various protein allergens from this dust mite have been identified, and the genes encoding the allergens cloned, including Der p 1, Der p 2, and Der p 5 proteins. Promoters that can be used to express the allergen in the bacterium include the erythromycin resistance gene promoter, IdhL promoter, or P25 promoter.

The invention further includes a method of decreasing the production of IgE in a subject (e.g., a mammal, such as a human) exposed to an allergen by administering to a subject a bacterium of the invention; and expressing the allergen in the subject in an amount sufficient to induce in the subject immunological tolerance to the allergen. The tolerance includes suppression of allergen-specific IgE production in the subject upon subsequent exposure to the allergen. In addition, the invention features a method of relieving bronchopulmonary inflammation in a subject exposed to an allergen by administering to a subject a bacterium of the invention; and expressing the allergen in the subject in an amount sufficient to relieve (i.e., decrease by a measurable amount) bronchopulmonary inflammation in the subject upon subsequent exposure to the allergen. The bacterium can be administered orally, sublingually, or intranasally.

A "lactic acid bacterium" as used herein refers to a gram-positive bacterium that is well known for its use in industrial food fermentations and for their probiotic properties. LAB and methods of the invention provide safe vaccines against allergies, especially allergies against dust mites. The high level of safety arises from the use of bacteria that are regularly and safely consumed by the general population.

An "allergen" is defined as a substance that cause a Type I immediate hypersensitivity reaction.

An "aeroallergen" is defined as having at least the following characteristics: specific antigenic groupings that evoke active reaginic responses, and ambient exposure levels to which can lead to overt tissue changes in sensitive subjects. Aeroallergens are airborne particles that can cause respiratory, cutaneous, or conjunctival allergy. The water-soluble portion of ragweed pollen, for example affects the respiratory and conjunctival mucosa, and the lipid-soluble allergens of ragweed pollen can cause a typical contact dermatitis on exposed skin.

A "probiotic" is a living microorganism that favorably influences the health of a host by improving the indigenous microflora of the host. There is no agreed set of selection criteria for classifying a viable bacterial strain as a probiotic. Common criteria used for isolating and defining probiotic bacteria and specific strains include the followings: (i) genera of human origin; (ii) stability against bile, acid, enzyme and oxygen; (iii) ability to adhere to intestinal mucosa; (iv) colonization potential in the human gastrointestinal tract; (v) production of antimicrobial substance; and (vi) demonstrable efficacy and safety.

"Yogurt" is defined as a coagulated milk product that results from fermentation of lactic acid in milk by *Lactobacillus bulgaricus* and *Streptococcus thermophilus.*

Allergic disorders treatable by the invention include rhinitis, sinusitis, asthma, hypersensitive pneumonia, extrinsic allergic alveolitis, conjunctivitis, urticaria, eczema, dermatitis, anaphylaxis, angioedema, allergic and migraine headache, and certain gastrointestinal disorders in which IgE-mediated allergy are involved.

Other features or advantages of the present invention will be apparent from the following detailed description, and also from the claims.

DETAILED DESCRIPTION

Figure 1:
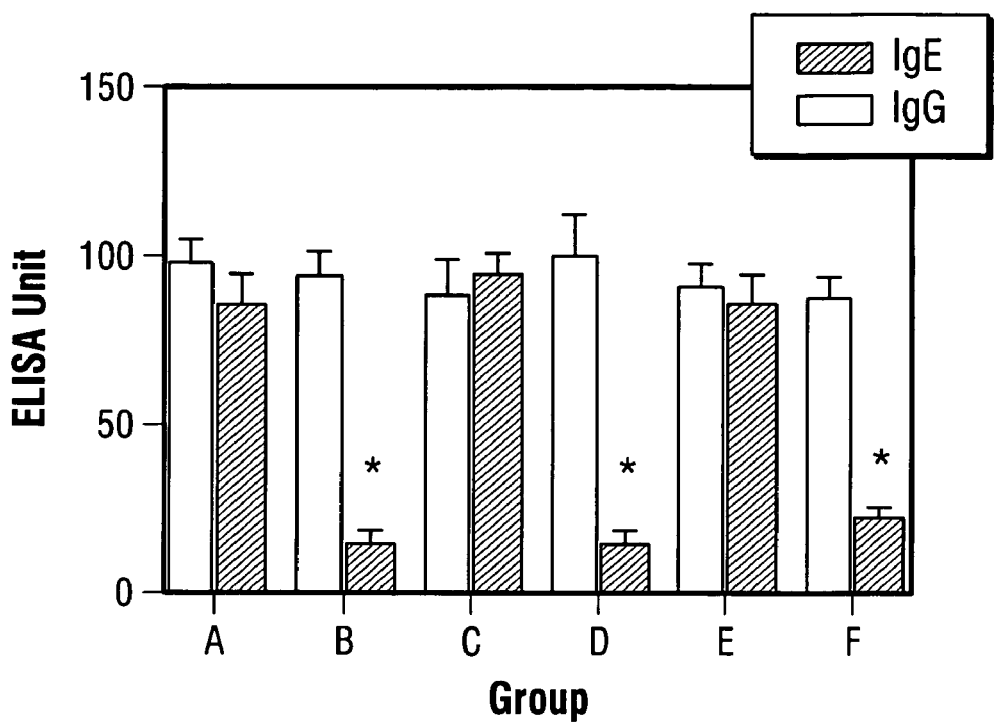
FIG. 1 is a bar graph showing allergen-specific IgE and IgG production in various groups of animals challenged with allergen. The composition of animal groups A–F are indicated in Table 1. Values expressed as mean±SEM (n=6). Asterisks represent statistical significance of p<0.01.

The invention relates to live allergen vaccines using lactic acid bacteria expressing one or more protein allergens.

Contemplated within the scope of this invention is the use of any suitable protein allergen, lactic acid bacterium, or expression vector, including any suitable promoter.

The specific allergen to be expressed for treating a particular allergy will of course depend on whether the undesirable immune response is targeted towards a protein allergen. Having identified a protein allergen that triggers the response, the skilled artisan can clone into a bacterial expression vector a nucleotide sequence encoding the allergen. This expression vector is then introduced into a lactic acid bacterium, which in turn is administered to an individual to ameliorate or prevent a subsequent symptom (e.g., skin inflammation or bronchopulmonary inflammation) characteristic of an allergy. Experimental protocols for evaluating and quantifying airway hyperreactivity is described below. Other methods of evaluating bronchopulmonary inflammation was well known in the art. Allergic asthma is characterized by both airway hyperreactivity and inflammation. Airway hyperreactivity can be measured by the changes of pulmonary test (invasive or non-invasive methods). Airway inflammation can be measured by the infiltration of inflammatory cells in the airway, especially eosinophils and neutrophils, and by changes in pathology. In some cases, it is not necessary to identify a single protein allergen. For example, multiple protein allergens from a single source can be used to induce immunological tolerance to the source (e.g., to treat an allergy against a food, such as shell fish, composed of different allergenic proteins). The multiple allergens can be expressed in the same bacterium (using one or more DNA vectors) or in different bacteria, each expressing a different allergen from the same source. In this situation, the skilled artisan need only know the discrete allergen source and two or more allergenic proteins present in the source.

Any lactic acid bacterium can be used in the invention, so long as they are amenable to genetic manipulation and heterologous protein expression. For example, several suitable species of Lactobacillus are described in Pouwels et al., J. Biotechnol. 44:183–192, 1996.

The experimental findings described herein led to the establishment of expression vector in lactic acid bacteria (LAB). Most commercial expression vectors are not suitable in the LAB. That is because only some promoters can work in a LAB. These promoters should constitutively driving expression of the allergen encoded by the gene. This allergen gene can be any clinically important allergen, especially aeroallergens. The invention can down-regulate allergic inflammation by suppression of the synthesis of allergen-specific IgE. Therefore this method can treat any IgE-mediated allergic disorders. The live vaccines can include one or more probiotics in any consumable or edible form such as yogurt.

For a further discussion of allergens and their physiological effects, see Aas et al., Allergy 33:3, 1978; Goldin et al., Br. J. Nut. 80:S203–S207, 1998; and Kailasapathy et al., J. Immunol. Cell Biol. 78:80–88, 2000.

Without further elaboration, it is believed that one skilled in the art can, based on the above disclosure, the efficacious treatment using live bacterial vaccines discussed below, utilize the present invention to its fullest extent. The following example is to be construed as merely illustrative of how one skilled in the art can produce and use live bacterial vaccines, and are not limitative of the remainder of the disclosure in any way. All publications cited in this disclosure are hereby incorporated by reference.

EXAMPLE

Methods and Material

DNA Manipulation. To obtain a promoter for expression of the Der p 5 gene in Streptococcus thermophilus and Lactobacillus acidophilus, two DNA fragments were generated by PCR. The primers used for this PCR were as follows. Primer PUC1233 is complementary to nucleotides 4119 to 4096 in pLP3537 and has the sequence CTTACGTCA CGTCTTGCGC (SEQ ID NO:1). pLP3537 and its nucleotide number are described in Posno et al., Appl. Env. Microbiol. 57:2764,2766, 1991. Primer PSD is identical to nucleotides 3658 to 3679 of pLP3537 and has the sequence AGATCTCCCTCTTTAAT TTGGTTATATG (SEQ ID NO:2). The additional six nucleotides at the 5' end of primer pSD was designed to yield a Bgl II site in the resulting PCR fragment.

Each PCR reaction mixture contained about 0.1 μg of plasmid pLP3537, 0.25 μg of each primer, 0.2 mM deoxynucleoside triphosphates, 1 U of Taq DNA polymerase, 10 mM Tris-HCl (pH 8.3), 50 mM KCl, 1.5 mM $MgCl_2$, and 0.01% (w/v) gelatin. The amplification included 30 cycles of 1 minute at 94° C., 2 minutes at 55° C., and 2 minutes at 72° C., using a MiniCycler (MJ Research; Watertown, Mass.). These reactions yielded a 0.4 kb DNA fragment with the primers. The DNAs were treated with Hind III (site present in primer PSD) and Bgl II, and agarose gel-purified. The DNA fragment was ligated with a Hind III-linearized plasmid pLP3537 and a 405 bp Hind III/Bgl II fragment of pCMVD, which is described in Hsu et al., Nature Medicine 2:540–544, 1996. The resulting plasmid pSDDerp5 contains and amplified fragment fused to the cDNA sequence encoding Der p 5.

Transformation. Bacterial strains were transformed by electroporation using the methods described in Walker et al., FEMS Microbiol. Lett. 138:233–237, 1996. The lactic acid bacteria transformed with pSDDerp5 were designated "LA-gm" for the transformed L. acidophilus and "ST-gm" for the transformed S. thermophilus. Non-transformed bacteria were designated "LA" and "ST," respectively Bacterial Cultures. L. acidophilus (ATCC 4356) was cultured on MRS broth and agar at 37° C. E. coli strain DH5α was maintained at 37° C. on LB broth and agar. The antibiotics ampicillin and erythromycin were purchased from Sigma (St. Louis). For selection of E. coli, ampicillin and erythromycin were used at concentrations of 50 and 50–100 μg/ml, respectively. For selection of L. acidophilus, erythromycin was used at 5 μg/ml. S. thermophilus (also obtained from ATCC) was cultured and treated in the same manner as for L. acidophilus.

Animals and Studies. Female BALB/c, ages 6 and 8 weeks, were obtained from the animal-breeding center of the College of Medicine, National Taiwan University (originally from Jackson Laboratory, Bar Harbor, Me.), were and divided into 6 groups for each experiment (Table 1).

TABLE 1

| Group | Number of Animals | Body Weight | Oral Vaccine |
| --- | --- | --- | --- |
| A | 6 | 33.3 ± 3.5 | $10^9$ LA |
| B | 6 | 32.6 ± 2.2 | $10^9$ LA-gm |
| C | 6 | 31.9 ± 1.5 | 100 μg Der p 5 |
| D | 6 | 31.5 ± 1.4 | 100 μg Der p 5 + $10^9$ LA-gm |

TABLE 1-continued

| Group | Number of Animals | Body Weight | Oral Vaccine |
|---|---|---|---|
| E | 6 | 32.2 ± 2.7 | $10^9$ ST |
| F | 6 | 33.4 ± 1.3 | $10^9$ ST-gm |

Animals were actively sensitized by intraperitoneal injection of 10 μg of recombinant Der p 5 that was purified as described in Lin et al., J. Allergy Clin. Immunol. 94:989–996, 1994. Mice received oral feeding of LA-gm or ST-gm for 3 days per week for 2 weeks. Twenty-one days after the sensitization, animals were exposed to an aerosol of either 0.1% of Der p 5-Glutathion S-transferase fusion protein for 20 min or PBS. Eight hours after inhalation challenge, pulmonary resistance was measured for 50 minutes, and the bronchoalveolar lavage fluids (BALF) and sera were collected.

Determination of Der p 5-specific IgG2a, and IgE. The amount of Der p 5-specific IgG2a and IgE was determined by ELISA as described in Hsu et al., Int. Immunol. 8:1405–1411, 1996. Protein binding plates were coated with 100 of purified Der p 5 (5 μg/ml) in coating buffer (0.1 M NaHCO$_3$, pH 8.2), as described in Hsu et al., Nature Medicine 2:540–544, 1996. After overnight incubation at 4° C., the plates were washed three times and blocked with 3% (w/v) BSA in PBS for 2 hours at 25° C. Test animal sera were diluted at 1: 100 for IgG measurements and 1:10 for IgE measurements. Each sample was analyzed in duplicate. After overnight incubation at 4° C., either biotin-conjugated rat anti-mouse IgE (Pharmingen, San Diego, Calif.) or rat anti-mouse IgG2a (Pharmingen) was diluted in 0.05% gelatin buffer and added to each test well for an additional hour. Avidin-alkaline phosphatase (Sigma Chemical Co., St Louis, Mo.) was diluted 1:1000, added to the wells, and incubated for 1 hour at 25° C. The wells were then washed six times.

The color reaction was developed by adding p-nitrophenylphosphate, disodium (Sigma). Plates were read in a microplate reader (Metertech, Taiwan) at 405 Readings were referenced to a standard serum pooled from 6 mice that were initially injected i.p. with 10 μg of Der p 5 in 4 mg of aluminum hydroxide and boosted 21 days with the same dose and formulation. This standard signal (positive control for antibody response) was normalized to 100 ELISA units per ml (see FIG. 1).

Non-invasive Determination of Airway Responsiveness. Using an apparatus for barometric whole body plethysmography (WBP; Buxco, Troy, N.Y.), the responses to inhaled methacholine in conscious, unrestrained mice were measured as described in Hamelmann et al., Am. J. Respir. crit. Care Med. 156:766–775, 1997. Methacholine is a drug known to increase airway resistance. Before taking readings, the box was calibrated with a rapid injection of 1 ml of air into the main chamber to obtain the 1 mv signal from the WBP device. Inspiration and expiration were recorded by establishing start-inspiration and end-inspiration, as the box pressure/time curve crossed the zero point. Start of an inspiration was determined by extrapolating from a straight line drawn from two levels of the rising inspiratory phase of the box pressure signal. Time of inspiration (Ti) was defined as the time from the start of inspiration to the end of inspiration. Time of expiration (TE) was defined as the time from the end of inspiration to the start of the next inspiration. The maximum box pressure signal occurring during one breath in a negative or positive direction was defined as the peak inspiratory pressure (PIP) or peak expiratory pressure (PEP), respectively. Recordings of every 10 breaths were extrapolated to define the respiratory rate in breaths per minute. The relaxation time (Tr) was defined as the time to reach 36% of the total expiratory pressure signal (area under the box pressure signal in expiration). This threshold served to correlate the decay time constant for the volume signal to the 36% decay of peak volume in passive expiration. Pause and enhanced pause ($P_{enh}$) was defined as follows.

Pause=$(Te-Tr)/Tr$ $P_{enh}=(PEP/PIP)\times$Pause

As an index of airway responsiveness, increases in $P_{enh}$ were measured. Mice were obtained and averaged for 3 min. Aerosolized saline, followed by increasing concentrations of methacholine (ranging from 1–100 mg/ml), was nebulized and inhaled for 3 minutes. Readings were taken and averaged for 3 minutes after each nebulization. Airway responsiveness was expressed as the $P_{enh}$ per dose methacholine.

Assessment of Cytokines in Bronchoalveolar Lavage Fluids (BALF). After measuring lung function as described above, mice were cannulated and lavaged with 5×0.5 ml aliquots of 0.9% sterile saline through a polyethylene tube introduced through a tracheotomy. Lavage fluid was centrifuged (500 g for 10 minutes at 4° C.), and the cell pellet was resuspended in 0.5 ml of Hank's balanced salt solution. Total cell counts were obtained by adding 10 μl of the cell suspension to 90 μl of 0.4% trypan blue and counted under a light microscope in a Newbauer chamber. Differentiated cell counts were made from cytospin preparations stained by Leu's stain. Cells were identified and differentiated into eosinophils, lymphocytes, neutrophils, and macrophages by visual inspection of standard morphologic differences. Five hundred cells were counted under 400× magnification, and the percentage and absolute number of each cell type were calculated.

Cytokine levels in BALF were measured by ELISA and expressed in pg/ml using standard curves for recombinant cytokines. Monoclonal Abs for capture and biotinylation were: R4-6A2 (name of capture antibody INF-γ) and XMG1.2 (name of biotinylated for INF-γ), available from PharMingen, San Diego, Calif.; and 11B11 (name of capture antibody for IL-4) and BVD6 (name of biotinylated for IL-4), available from PharMingen. The limits of detection were 18 pg/ml.

Statistical Analysis. ANOVA was performed to compare the differences among groups. Following analysis of variance, the Duncan multiple range test was used to differentiate differences between experimental and control groups. A p<0.05 was considered statistically significant.

Results

Inhibition of Allergen-Specific IgE Response In Vivo. Mice receiving vehicle (non-recombinant bacteria), pSD-Derp5-transformed bacteria, and recombinant Der p 5 were sensitized intraperitoneally with allergen Der p 5 one week before vaccine administration and challenged via inhalation at 3 weeks after sensitization. The presence of anti-Der p 5 IgE in the serum 3 weeks after allergen challenge was assayed using ELISA. The results are summarized in FIG. 1. Der p 5-specific IgE increased significantly in the vehicle-treated group. In contrast, pSDDerp5-treated mice exhibited more than 80% inhibition of Der p 5-specific IgE synthesis. The inhibition of IgE synthesis by gene-modified lactic acid bacteria was specific to Der p 5 allergen, because in a separate experiment pSDDerp5-treated mice challenged with Der p 2 could still produce Der p 2-specific IgE. Thus, direct oral feeding of allergen-expressing lactic acid bacteria could efficiently inhibit an allergen-specific IgE production. Furthermore, this suppressive effect was far superior to oral feeding with recombinant allergen alone (see Group C in FIG. 1), and the inclusion of recombinant allergen in the vaccine did not measurably increase the effect of orally administering allergen-expressing bacteria alone (compare Groups B and D). There was no significant difference Der p 5-specific IgG2a production among the experimental groups.

is correlated with airway inflammation. Both airway hyperactivity inflammation are features of allergic asthma.

Figure 3:
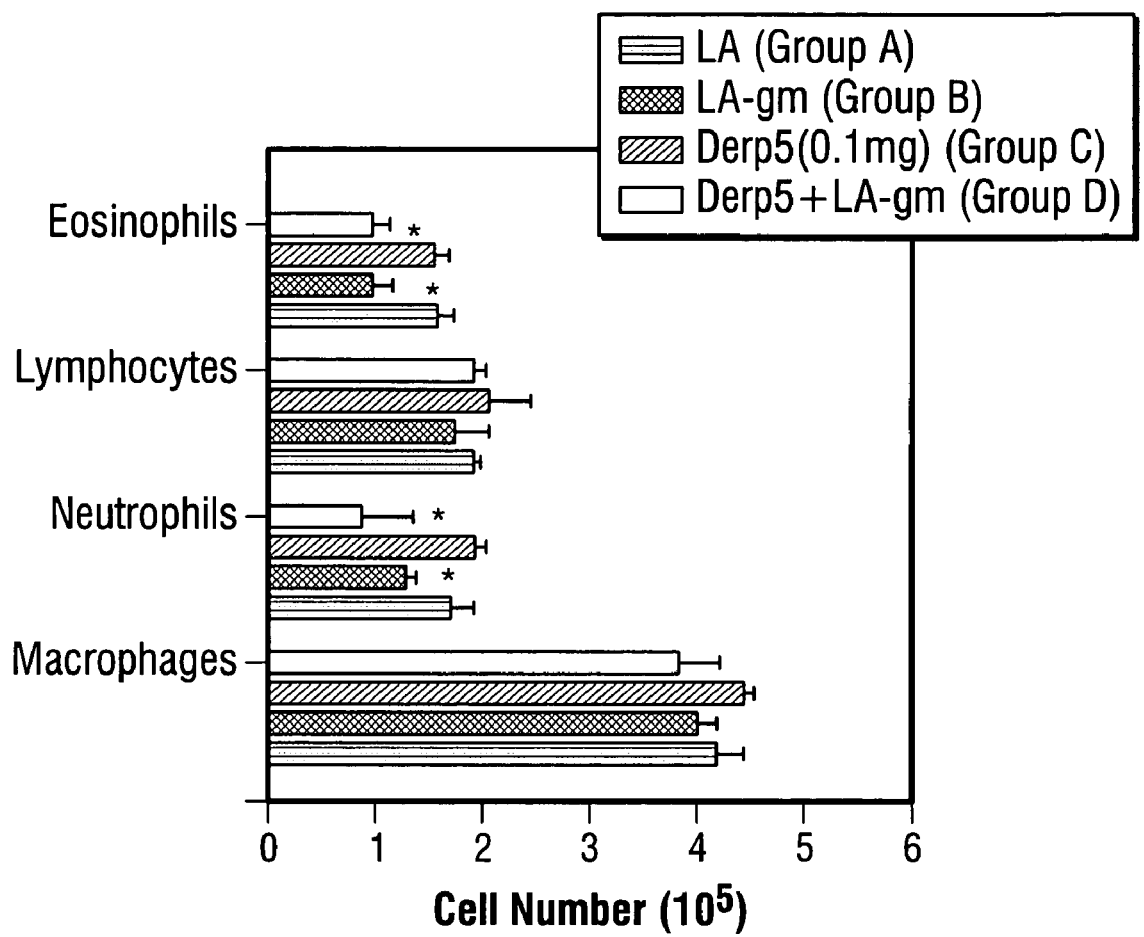
FIG. 3 is a bar graph showing numbers of different types of white blood cells in animals receiving different vaccines and challenged with allergen. Values expressed as mean±SEM (n=6). Asterisks represent statistical significance of p<0.05.

Vaccine Effect on Bronchoalveolar Cell Number. The numbers of cells in the bronchoalveolar lavage (BALF) after challenge was used as a measure of cell infiltration into the bronchopulmonary tract in response to exposure to allergen (FIG. 3). There were significantly lower numbers of eosinophils and neutrophils in the BALF of animals receiving bacteria expressing allergen (Groups B and D), as compared to vehicle-treated Groups A and recombinant allergen-treated Group B (p<0.05). The numbers of macrophages and lymphocytes were not significantly different among the experimental groups. Therefore, Der p 5 challenge induced infiltration of eosinophils and neutrophils, and this infiltration can be significantly inhibited by a live lactic acid bacterial vaccine.

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Primer for PCR

<400> SEQUENCE: 1
cttacgtcac gtcttgcgc                                                19

<210> SEQ ID NO 2
<211> LENGTH: 28
<212> TYPE: DNA
<213> ORGANISM: Artificial Sequence
<220> FEATURE:
<223> OTHER INFORMATION: Primer for PCR

<400> SEQUENCE: 2
agatctccct ctttaatttg gttatatg                                      28
```

Figure 2:
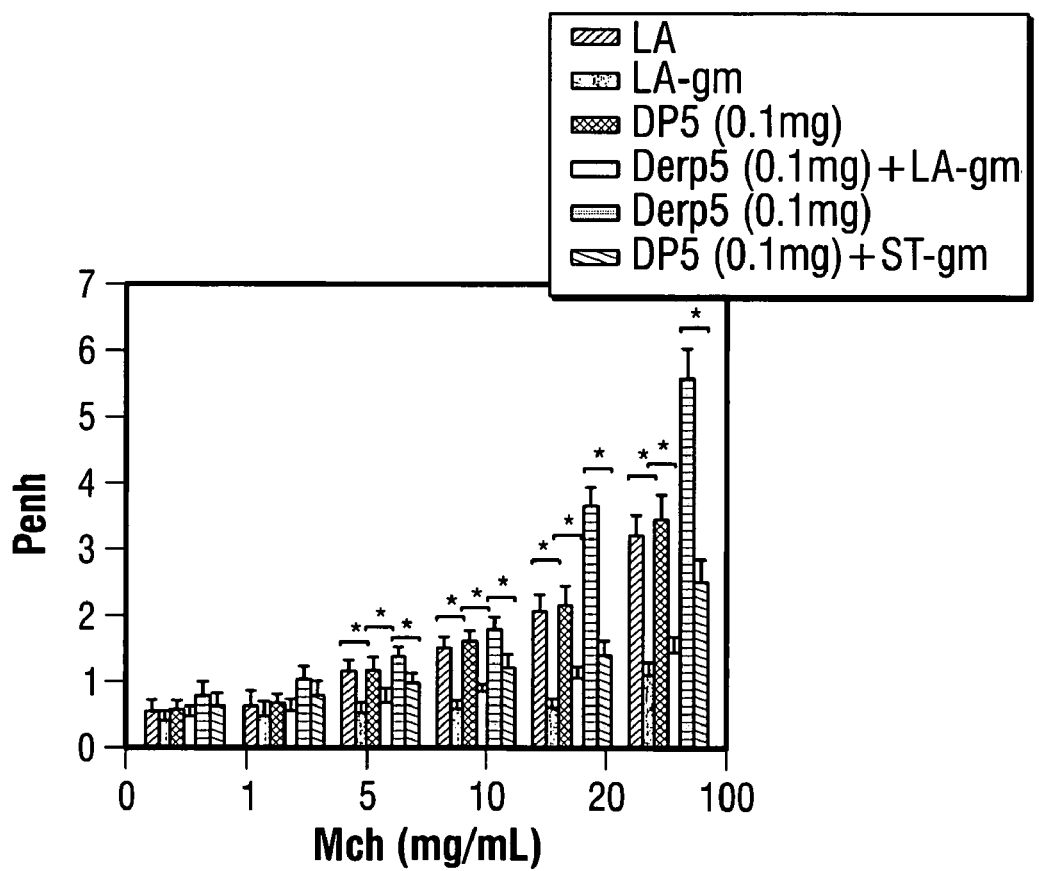
FIG. 2 is a bar graph showing $P_{enh}$ for animals receiving different vaccines and treated with different concentrations of methacholine (Mch). Values expressed as mean ±SEM (n=3). Asterisks represent statistical significance of p<0.05.

Suppression of Airway Hyperreactivity (AHR) In Vivo. The efficacy and specificity of live lactic acid bacterial vaccines was evaluated using measures of airway (bronchopulmonary) hyperreactivity. The airway response to aerosolized methacholine was measured in conscious, unrestrained mice 8 hours after last inhalation challenge. For all mice, a complete dose-response curve to methacholine raging from 1 to 100 mg/ml was obtained. In all groups of mice, no significant differences were observed in the basal $P_{enh}$ and saline aerosol-induced $P_{enh}$ values. In negative vaccine controls animals (Groups A, C, and E), Der p 5 challenge induced a significant increase in airway responsiveness to methacholine compared with the baseline. In contrast, treatment with LA-gm or ST-gm (Groups B, Group D, and Group F) significantly inhibited AHR at doses ranging from 10 to 100 mg/ml methacholine (FIG. 2). Thus Der p 5-induced AHR can be abolished by the administration of allergen-expressing lactic acid bacteria.

An increase in airway resistance after methacholine challenge is correlated with airway hyperactivity. An increase in cell infiltration (e.g., neutrophil and eosinophil infiltration)

What is claimed is:

1. A method of decreasing the production of IgE in a subject exposed to a dust mite allergen, the method comprising:
    orally administering to the subject a non-pathogenic, Gram-positive bacterium that comprises (i) a nucleotide sequence that encodes a dust mite allergen and (ii) a promoter operably linked to the nucleotide sequence, wherein the promoter is functional in the non-pathogenic, Gram-positive bacterium; and
    thereby expressing the allergen in the non-pathogenic, Gram-positive bacterium while said bacterium is in the subject in an amount sufficient to suppress an allergen-specific IgE production in the subject upon subsequent exposure to the allergen.

2. The method of claim 1 in which the bacterium is of the genus *Lactobacillus, Streptococcus,* or *Bifidobaterium*.

3. The method of claim 2 in which the bacterium is of the genus *Lactobacillus*.

4. The method of claim 3 in which the bacterium is *Lactobacillus acidophilus*.

5. The method of claim 1 in which the dust mite allergen is an allergen of *Dermatophagoides pteronyssinus, D. fari-*

*nae, D. microceras, Tyrophagus putesentiae, Lepidoglyphus domesticus, L. destructor, Acarus siro, Euroglyphus maynei,* or Biomia tropicali.

6. The method of claim 5 in which the dust mite allergen is an allergen of *Dermatophagoides pteronyssinus.*

7. The method of claim 1, wherein the allergen is a protein allergen.

8. The method of claim 1, wherein the allergen is a Der p 5 allergen.

9. The method of claim 6 in which the allergen is Der p 5.

10. The method of claim 1, wherein the promoter is a constitutive promoter.

11. The method of claim 3, wherein the bacterium is administered in a yogurt.

12. A method of decreasing the production of IgE in a subject exposed to a dust mite allergen, the method comprising:

orally administering to of subject a lactic acid bacterium that expresses a dust mite allergen; and thereby expressing the allergen in the lactic acid bacterium while the lactic acid bacterium is in the subject in an amount sufficient to suppress an allergen-specific IgE production in the subject upon subsequent exposure to the allergen.

13. The method of claim 12 in which the dust mite allergen is an allergen of *Dermatophagoides pteronyssinus, D. farinae, D. microceras, Tyrophagus putesentiae, Lepidoglyphus domesticus, L. destructor, Acarus siro, Euroglyphus maynei,* or *Biomia tropicali.*

14. The method of claim 12 in which the dust mite allergen is an allergen of dust mite of *Dermatophagoides* genus.

15. The method of claim 12 in which the bacterium belongs to the *Lactobacillus* genus.

16. The method of claim 15 in which the bacterium is administered as a yogurt composition.

17. The method of claim 12 in which the subject is a human subject.

18. A method of decreasing the production of IgE in a subject exposed to a protein aeroallergen, the method comprising:

orally administering to the subject a non-pathogenic, Gram-positive bacterium that comprises (i) a nucleotide sequence that encodes a protein aeroallergen and (ii) a promoter operably linked to the nucleotide sequence, wherein the promoter is functional in a bacterial cell; and thereby expressing the protein aeroallergen in the non-pathogenic, Gram-positive bacterium while said bacterium is in the subject in an amount sufficient to suppress an aeroallergen-specific IgE production in the subject upon subsequent exposure to the protein aeroallergen.

19. A method of alleviating bronchopulmonary congestion in a subject exposed to a dust mite allergen, the method comprising:

orally administering to the subject a lactic acid bacterium that expresses a dust mite allergen; and thereby expressing the allergen in the lactic acid bacterium while the lactic acid bacterium is in the subject in an amount sufficient to alleviate bronchopulmonary congestion in the subject upon subsequent exposure to the dust mite allergen.

20. The method of claim 19 in which the bacterium belongs to the *Lactobacillus* genus, and the dust mite allergen is *Dermatophagoides pteronyssinus.*

21. The method of claim 1, 3, 4, or 6 wherein the promoter is the erythromycin resistance gene promoter, IdhL promoter, or P25 promoter.

22. The method of claim 20 wherein the bacterium is *Lactobacillus acidophilus.*

23. The method of claim 18 wherein the protein aeroallergen is a protein component of a pollen, mold, animal dander, or insect.

24. The method of claim 1 or 18 wherein the bacterium can adhere to intestinal mucosa.

* * * * *